United States Patent [19]

Reynolds et al.

[11] Patent Number: 5,849,017
[45] Date of Patent: Dec. 15, 1998

[54] MOULDED PLASTIC OBSTETRIC FORCEPS

[75] Inventors: J. Lawrence Reynolds; Paul M. Kurowski, both of London, Canada

[73] Assignee: The University of Western Ontario Stevenson-Lawson Building, London, Canada

[21] Appl. No.: 715,824

[22] Filed: Sep. 19, 1996

[51] Int. Cl.⁶ .......................... A61G 17/42; A61G 17/46
[52] U.S. Cl. .................. 606/122; 606/119; 606/205; 606/206
[58] Field of Search .................... 606/122, 119, 606/120, 124, 121, 205, 206, 208; 81/319, 320, 341, 417

[56] References Cited

U.S. PATENT DOCUMENTS

| | | | |
|---|---|---|---|
| 451,930 | 5/1891 | Hamilton | 606/122 |
| 2,637,320 | 5/1953 | Greenberg | 606/122 |
| 3,088,465 | 5/1963 | Smith | 606/122 |
| 3,183,911 | 5/1965 | Anglemyer | 606/124 |
| 3,785,381 | 1/1974 | Lower et al. | 606/122 |
| 3,789,849 | 2/1974 | Laufe et al. | 606/122 |
| 3,789,949 | 2/1974 | Laufe et al. | 606/122 |
| 5,019,091 | 5/1991 | Porat et al. | 606/210 |
| 5,595,569 | 1/1997 | Hebbard | 606/131 |
| 5,599,350 | 2/1997 | Schulze et al. | 606/51 |
| 5,674,243 | 10/1997 | Hale | 606/119 |

FOREIGN PATENT DOCUMENTS

| | | | |
|---|---|---|---|
| 388681 | 1/1924 | Germany | 606/122 |
| 42 35 442 A 1 | 4/1994 | Germany . | |

OTHER PUBLICATIONS

Gynecology, Obstetrics–GL, Obstetrical Forceps, Mueller & Co., p. 227, 1963.

Primary Examiner—Richard J. Apley
Assistant Examiner—Justine R. Yu
Attorney, Agent, or Firm—Gowling, Strathy & Henderson

[57] ABSTRACT

Obstetric forceps have a pair of elongated members, each having a blade at one end, a handle at an opposite end and a shank connecting the blade and handle. The members pivotally engage each other at a pivot point intermediate their ends and freely moveable when so engaged. The blades and shanks of each of the members are resiliently constructed to exert a traction force within a preset margin of safety and to slip when the preset margin of safety is exceeded.

8 Claims, 6 Drawing Sheets

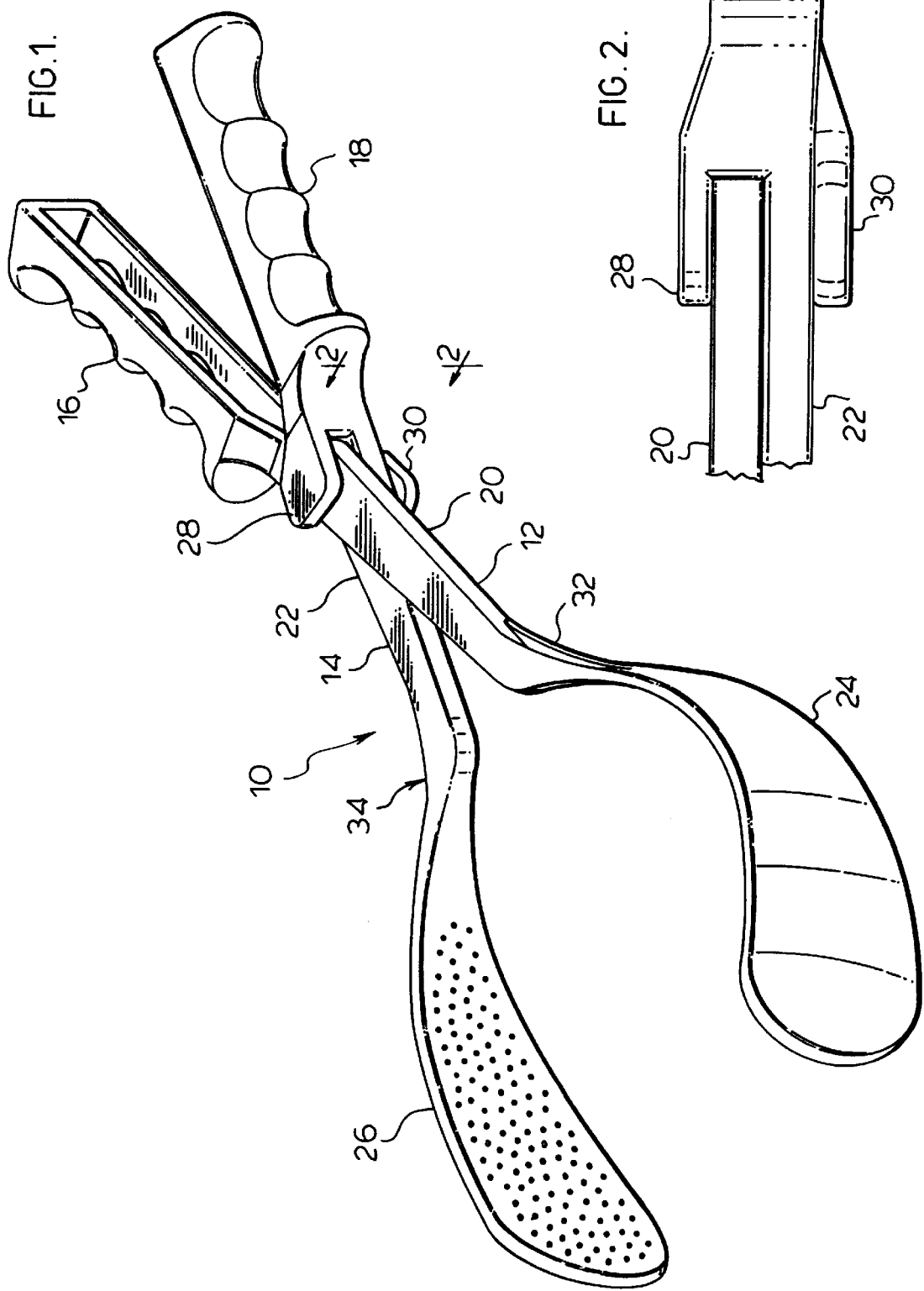

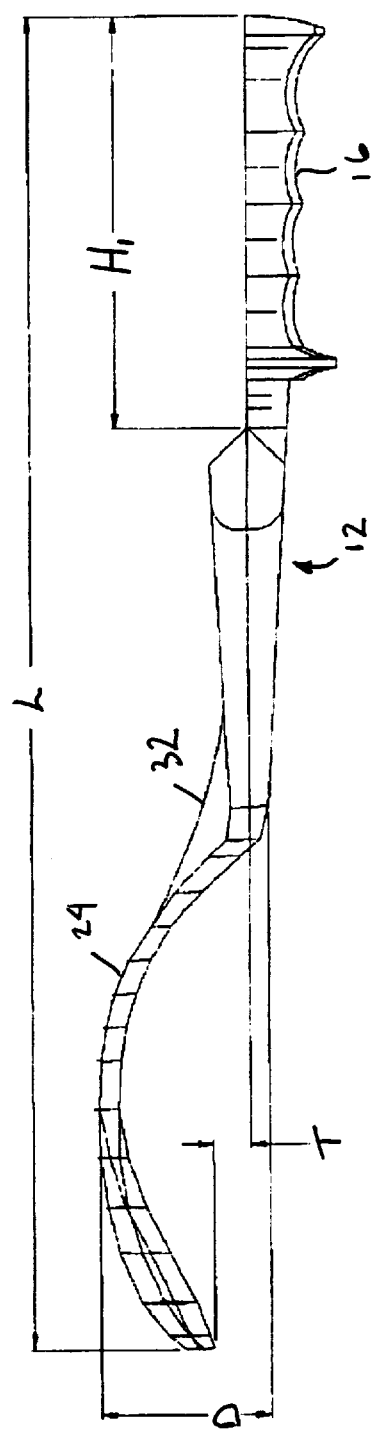
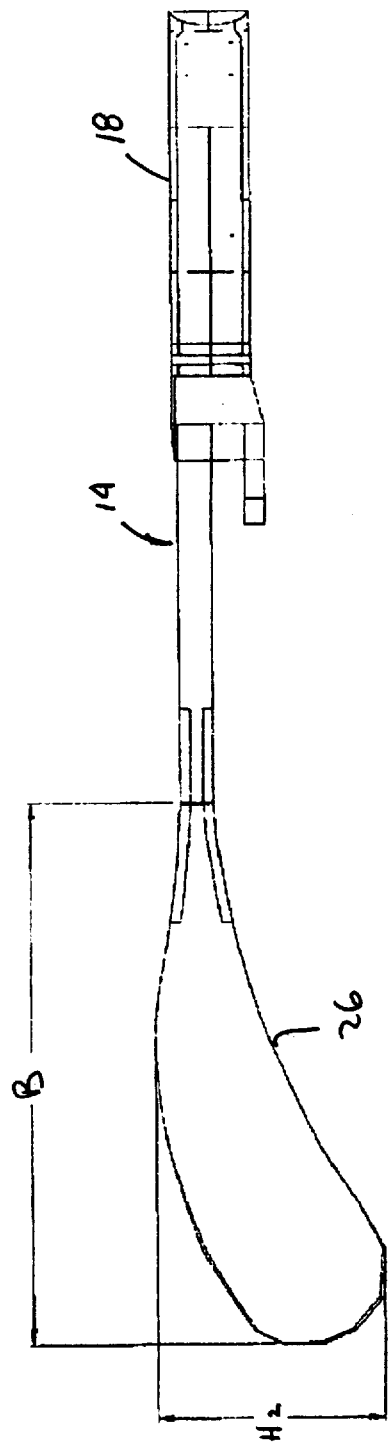
Fig. 8
Fig. 9

MOULDED PLASTIC OBSTETRIC FORCEPS

FIELD OF INVENTION

This invention relates to a moulded plastic obstetric forceps. In particular, this invention relates to obstetric forceps having blades which are made of a material that is rigid enough to exert traction within a preset margin of safety and flexible enough to slip when the preset margin of safety is exceeded.

BACKGROUND TO THE INVENTION

Obstetric forceps have been used to assist women during childbirth for the past several hundred years. The basic design has changed little over that period of time. There are, however, hundreds of separately modelled, designed and patented obstetric forceps.

Obstetric forceps work by grasping the baby's head while the baby is still within the body of its mother. The forceps are then used to either turn the baby's head into a position where the baby's head can be born more easily and/or through exerting tractional force to help to pull the baby's head down through the birth canal effecting delivery.

The present procedure carries risks to the mother and child because obstetric forceps are made of unyielding stainless steel. This can result in maternal injuries and fetal injuries. These injuries occur from compressive forces of the forceps pressing on the fetal head which may result in brain injuries, scalp or face injuries. Because of the unyielding nature of stainless steel obstetric forceps, the only safety factor is the skill of the birth attendant.

Several attempts have been made to prevent the birth attendant from applying too much pressure to the fetal head. Such attempts include mounting a pressure sensor on the blade portion of the forceps to indicate the pressure being applied and having a shiftable handle which will disengage after a pre-set force has been exceeded. (U.S. Pat. No. 3,785,381 and 3,789,949, respectively) In the first case, the forceps does not prevent applying an excessive force; it merely indicates when one is being applied. The skill of the birth attendant is still a principal factor in the safe use of the forceps. In the latter case, the mechanism for restricting the compressive forces is complicated making it relatively expensive to manufacture and maintain.

SUMMARY OR THE INVENTION

The disadvantages of the prior art may be overcome by providing obstetric forceps having blades contoured to accommodate a head of the baby and the unique architecture of the maternal pelvis and comprising a contoured material that is rigid enough to exert traction within a preset margin of safety and flexible enough to slip when the preset margin of safety is exceeded.

According to one aspect of the invention, there is provided obstetric forceps comprising a pair of elongated members. Each of the members has a blade at one end, a handle at an opposite end and a shank connecting the blade and handle. The members pivotally engage each other at a pivot point intermediate their ends and are freely moveable when so engaged. The blades and shanks of each of the members are resiliently constructed to exert a traction force within a preset margin of safety and to slip when the preset margin of safety is exceeded.

According to another aspect of the invention, there is provided obstetric forceps comprising a pair of elongated members molded from a glass filled polycarbonate material. Each of the members has a blade at one end, a handle at an opposite end and a shank connecting the blade and handle. A reinforcing gusset extends from the shank to an outside surface of the blade for limiting flexure of the blade relative to the shank. The members pivotally engage each other at a pivot point intermediate their ends and are freely moveable when so engaged. The blades and shanks of each of the members are resilient to exert a traction force within a preset margin of safety and to slip when the preset margin of safety is exceeded. The design of the members and the material thereof allow for the flexure of the blade and shank to be linearly proportional to the magnitude of the traction force.

DESCRIPTION OF THE DRAWINGS

In drawings which illustrate the preferred embodiment of the invention,

FIG. 1 is a perspective view of the obstetric forceps of the present invention;

FIG. 2 is a partial side elevational view of the obstetric forceps of FIG. 1, illustrating the pivotal connection;

FIG. 8 is a plan view of one forcep member of the obstetric forceps of FIG. 1; and FIG. 9 is a side elevational view of the other forcep member of the obstetric forceps of FIG. 1.

DESCRIPTION OF THE INVENTION

Figure 3:
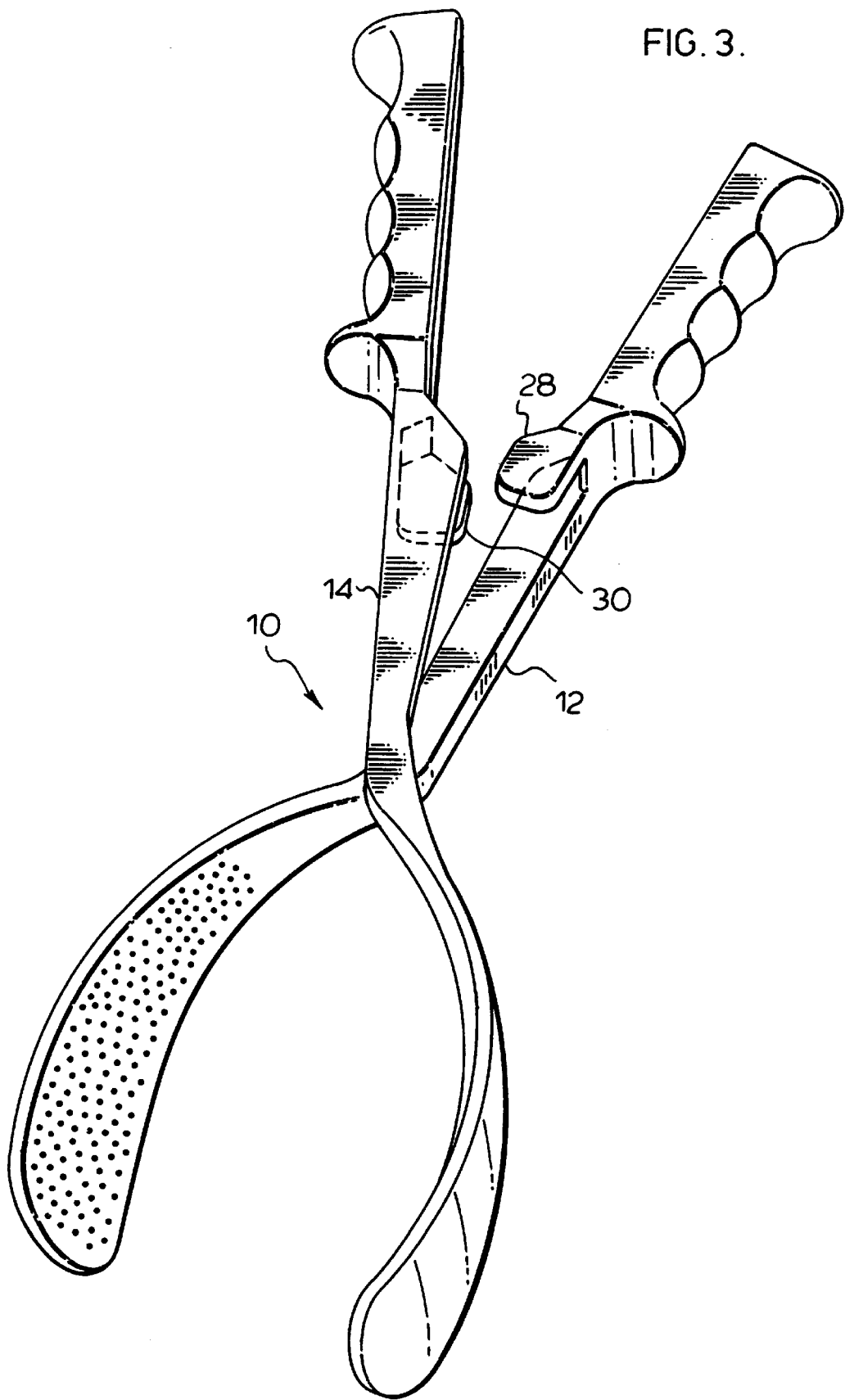
FIG. 3 is a perspective view of the obstetric forceps of FIG. 1, illustrating the forceps in a partially separated condition.

Referring to FIG. 1, the obstetric forceps 10 of the present invention are illustrated. The forceps 10 includes elongate members 12 and 14 pivotally engaging each other at an intermediate point. Elongate members 12 and 14 are identical to each other except that one is a right hand member and the other is a left hand member.

Elongate members 12 and 14 each has a handle 16 and 18, a shank 20 and 22 and a blade 24 and 26. Handles 16 and 18 have a surface contoured to complement a hand and fingers for facilitating gripping by a hand. At the head of each of the handles 16 and 18, each shank has a tab 28 and 30.

Figure 4:
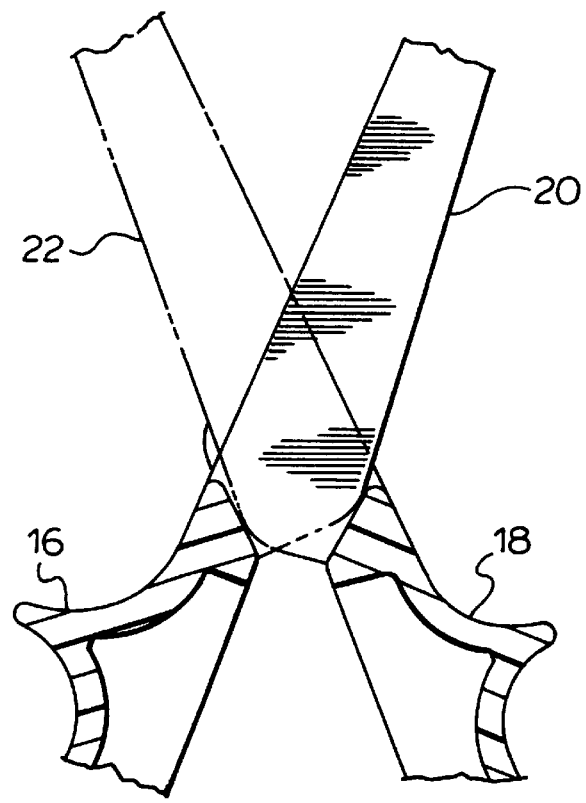
FIG. 4 is a partial sectional top plan view of the obstetric forceps of FIG. 1 along the lines 1—1, illustrating the pivotal connection.

Referring to FIGS. 2, 3 and 4, tabs 28 and 30 are spaced from and extend parallel to the shanks 20 and 22, respectively. The spacing of the tabs 28 and 30 is approximately the same distance as the thickness of the shanks 20 and 22. The base of each tab 28 and 30 is diagonal to the longitudinal axis of the elongate members 12 and 14. In a manner well known in the art, the shanks 20 and 22 and tabs 28 and 30 interlock with each other to pivotally engage the elongate members 12 and 14. The interlock permits free pivotal movement between the elongate members 12 and 14 while allowing free separation of the members.

Figure 5:
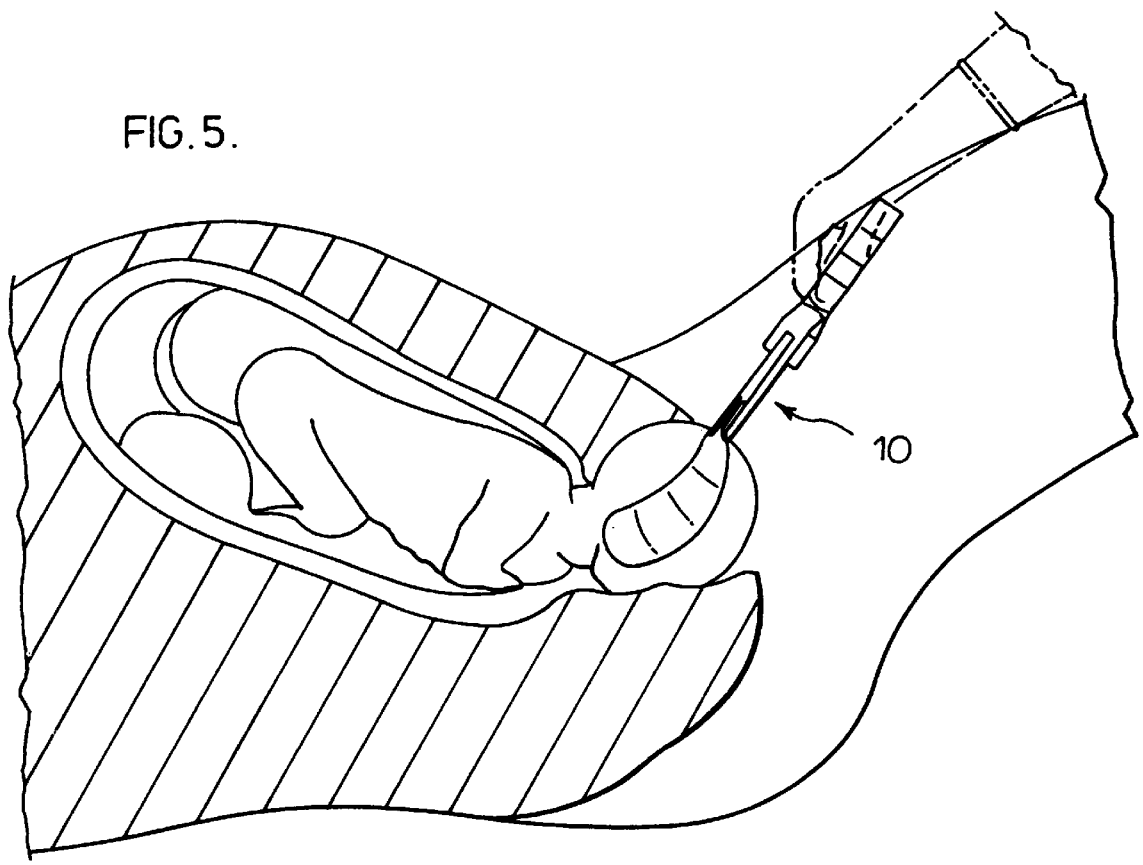
FIG. 5 is a partial sectional view of a maternal pelvis showing the obstetric forceps of FIG. 1 gripping a fetal head.
Figure 6:
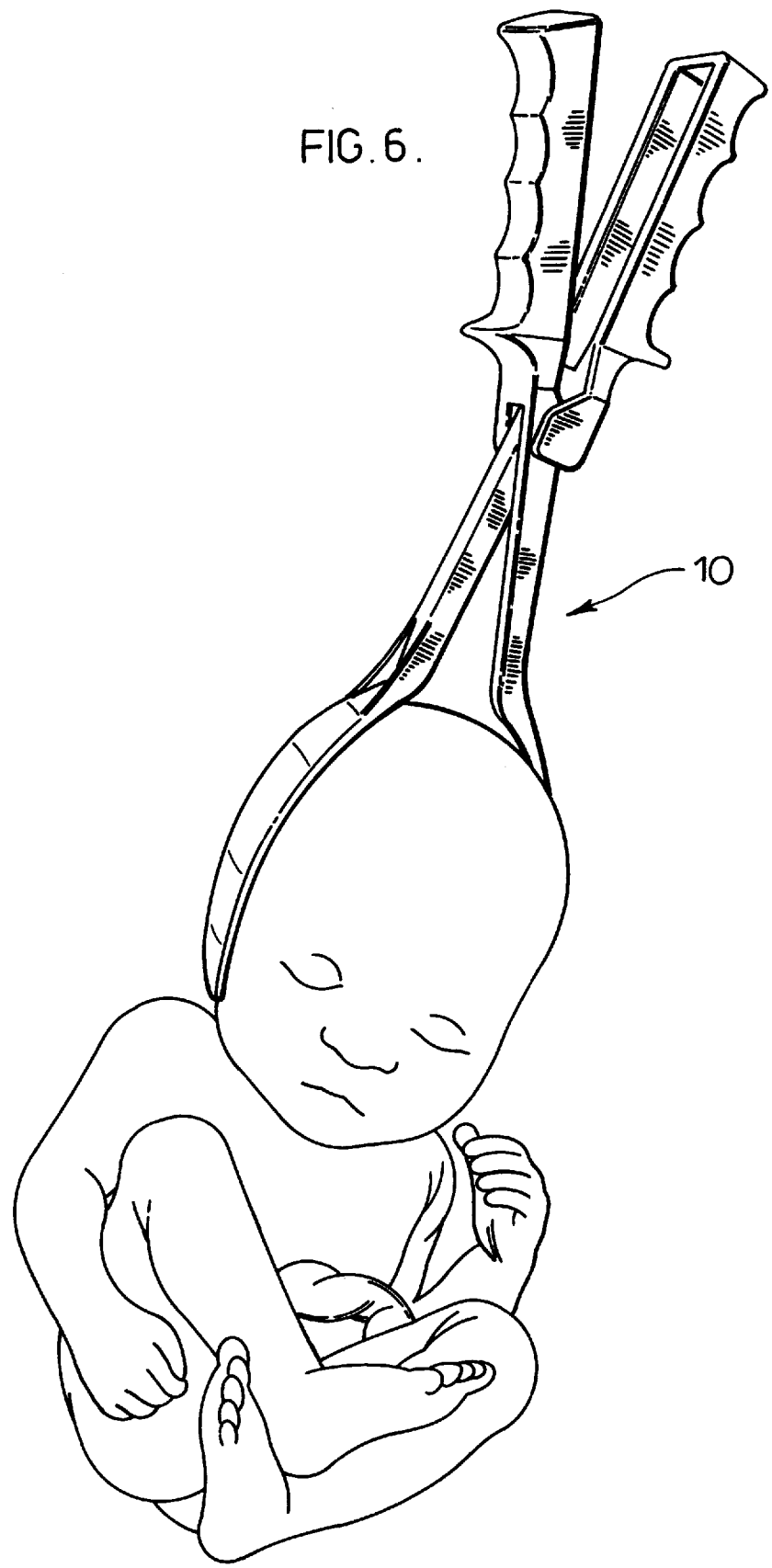
FIG. 6 is a perspective view of the obstetric forceps of FIG. 1 gripping a fetal head.

Blades 24 and 26 are smoothly curved for engaging a baby's head as illustrated in FIGS. 5 and 6. The inner surface of the forceps blades 24 and 26 that are applied to the baby's head carry a unique design. The inner surface of the forceps blades are finely textured rather than being completely smooth. The textured surface reduces inappropriate slippage. The design assists in gripping the baby's head and to promote drainage of fluids from the area of contact resulting in better traction without minimizing the safety flexibility of the above mentioned forceps.

The shanks 20 and 22 merge with the blades 24 and 26. Gussets 32 and 34 extend from shanks 20 and 22 to the outside surface of the blades 24 and 26, respectively. The gussets 32 and 34 reinforce the transition between the shanks 20 and 22 and the blades 24 and 26. The gussets 32 and 34 improve the rigidity of the blades 24 and 26 and also ensure a generally linear relationship between the traction force appliable and the flexure of the members 12 and 14.

The material characteristics, size, length and shape of the elongated members 12 and 14 are important for the safe use of the forceps of the present invention. Referring to FIGS. 8 and 9 and by way of example only, the overall length L of the forceps is 405 mm. The handles 16, 18 extend a distance H1 of 126 mm while the blades 24, 26 extend a distance B of 165 mm. The blades 24, 26 each has a maximum depth of curvature D of 51 mm and a maximum height H2 of 68 mm. The maximum depth of curvature D is measured viewing the members 12 and 14 in plan, from a longitudinal axis extending through the base of the blade and perpendicular to the peak. The maximum height H2 is measured viewing the members 12 and 14 in side elevation. The distal tip of each blade 24, 26 is spaced a distance T of 11 mm from the central longitudinal axis of each elongate member 12, 14.

Figure 7:
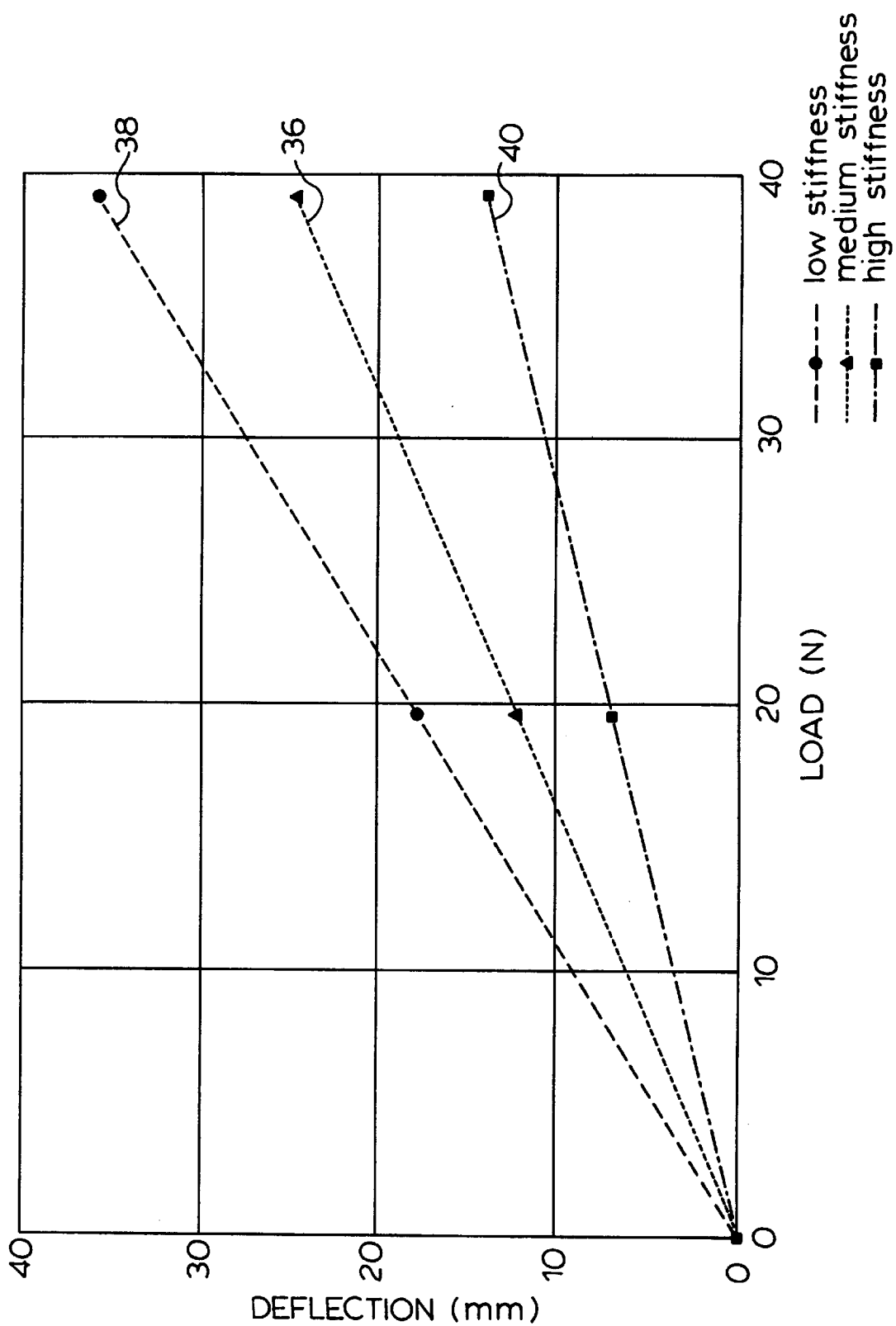
FIG. 7 is a graph illustrating blade stiffness relationship of the forceps of FIG. 1.

As illustrated in FIG. 7, the members 12 and 14 have a linear relation between the pressure load appliable by the blades 24 and 26 and the amount of deflection at the tip of the blades 24 and 26 relative to the pivot point of the members 12 and 14. The line 36 illustrates the preferred load-deflection function, while line 38 illustrates a high margin of safety, i.e. given loads will result in larger deflection allowing lesser traction forces to be applied, and line 40 illustrates a low margin of safety, i.e given loads will result in less deflection allowing greater traction forces to be applied. The preferred rate of deflection as represented by line 36 is about 0.6 mm/N, while the high margin of safety as represented by line 38 is about 0.9 mm/N and the low margin of safety as represented by line 40 is about 0.3 mm/N.

In the preferred embodiment, the elongated members 12 and 14 are each molded as an integral part. The members 12 and 14 are molded preferably using a glass filled polycarbonate plastic. The preferred material has 40% short glass fiber filled and is similar to material available under the brand name and designation THERMOCOMP DF-1008 EM MR polycarbonate.

The use of glass filled polycarbonate plastic material gives the forceps 10 certain unique qualities. First, the forceps 10 are flexible and will mold to the baby's head. Second, the forceps 10 will flex in a known relationship with the traction force applied. Accordingly, once a predetermined of force has been applied, forceps 10 will slide off the baby's head preventing fetal or maternal injury.

In use, the forceps 10 of the present invention are applied in the traditional fashion to the baby's head and the traditional form of traction and the rotation applied. If tractional forces within a safety margin are exceeded, forceps 10 will slip off. In this situation where birth is unable to be accomplished by these forceps, births would then be accomplished by cesarean section. If however, the birth is assisted through the forceps 10, the forceps will then be removed once the baby's head has been fully born from the body of the child's mother.

The forceps 10 are then discarded as the cleaning and sterilization process may change the tensile and flexure qualities of the forceps and render them less safe or prone to fracture.

It is now apparent to a person skilled in the art that the obstetric forceps of the present invention could be readily modified. It is understood that certain changes in style, size and components may be effective without departure from the spirit of the invention and within the scope of the appended claims.

We claim:

1. Obstetric forceps comprising:

a pair of elongate members, each of which has a blade at one end, a handle at an opposite end and a shank connecting said blade and handle, said members pivotally engaging each other at a pivot point intermediate their ends, each said blade having a blade tip distal said handle and said members being sized and constructed of a resilient material such that resilient deflection of the blade tip relative to the pivot point occurs when a pressure load is applied to said blades as they are closed on a head of a baby, said deflection being in the range of from about 0.3 mm/N to about 0.9 mm/N to allow the blades to slip off said head of a baby during traction thereof if said pressure load exceeds a preset margin of safety.

2. Obstetric forceps as claimed in claim 1 wherein said blades and shanks are molded with a glass filled polycarbonate plastic.

3. Obstetric forceps as claimed in claim 2 wherein said glass filled polycarbonate plastic includes about 40% short glass fiber.

4. Obstetric forceps as claimed in claim 1 further including a gusset at the connection between each said shank and each said blade, each said gusset reinforcing its respective connection.

5. Obstetric forceps as claimed in claim 4 wherein each said gusset extends from its respective shank to an outside surface of its respective blade for limiting flexure of said blade relative to said shank.

6. Obstetric forceps as claimed in claim 1 wherein said deflection is in the range of from about 0.6 mm/N to about 0.9 mm/N.

7. Obstetric forceps as claimed in claim 1 wherein said deflection is about 0.6 mm/N.

8. Obstetric forceps as claimed in claim 1 wherein adjacent surfaces of said blades include a textured surface.

* * * * *